United States Patent
Ervin

(10) Patent No.: US 10,223,504 B2
(45) Date of Patent: Mar. 5, 2019

(54) METHOD, SYSTEM AND APPARATUS FOR MEDICATION THERAPY MANAGEMENT PROGRAMS

(71) Applicant: MEDICASAFE, INC., New York, NY (US)

(72) Inventor: Matthew James Ervin, New York, NY (US)

(73) Assignee: MEDICASAFE, INC, New York, NY (US)

( * ) Notice: Subject to any disclaimer, the term of this patent is extended or adjusted under 35 U.S.C. 154(b) by 540 days.

(21) Appl. No.: 14/389,025

(22) PCT Filed: Apr. 3, 2013

(86) PCT No.: PCT/US2013/035159
§ 371 (c)(1),
(2) Date: Sep. 29, 2014

(87) PCT Pub. No.: WO2013/152128
PCT Pub. Date: Oct. 10, 2013

(65) Prior Publication Data
US 2015/0058041 A1    Feb. 26, 2015

Related U.S. Application Data

(60) Provisional application No. 61/619,880, filed on Apr. 3, 2012.

(51) Int. Cl.
*G06F 19/00* (2018.01)
*G06Q 50/22* (2018.01)
(Continued)

(52) U.S. Cl.
CPC ........ *G06F 19/3462* (2013.01); *A61J 7/0084* (2013.01); *A61J 7/0481* (2013.01);
(Continued)

(58) Field of Classification Search
CPC .. G06F 19/3462; G06F 19/326; A61J 7/0084; A61J 7/0481; G16H 10/60
(Continued)

(56) References Cited

U.S. PATENT DOCUMENTS 8,478,604 B2* 7/2013 Henderson ............ G06F 19/325
                                                      705/2
2002/0169635 A1* 11/2002 Shillingburg ....... G06F 19/3462
                                                      705/2

(Continued)

FOREIGN PATENT DOCUMENTS

EP      1038798 A2    9/2000
WO    2010/054205     5/2010

OTHER PUBLICATIONS

International Search Report and Written Opinion of the International Searching Authority for PCT/US2013/035159 dated Jul. 11, 2013.

(Continued)

*Primary Examiner* — Hiep V Nguyen
(74) *Attorney, Agent, or Firm* — Myers Wolin, LLC

(57) ABSTRACT

A method, system and apparatus for medication therapy management programs. One embodiment of the invention includes a comprehensive, technology-enhanced pharmacy system for patients following a complex medication to regimen comprising a treatment database, communications interface, and a personal medication cartridge configured to store medication and configured based on a treatment optimization algorithm. Another embodiment of the invention includes a medication administration apparatus comprising computer processing hardware, a user interface, an interface for receiving a personal medication cartridge including medication dose packets labeled with computer-readable identification or an RFID mechanism, a medication ejection mechanism, and a medication dispensing sensor. The medi- (Continued)

cation administration apparatus utilizes medication dose packets and prescription information and identifies individual dose packets using computer-readable information or an RFID mechanism. The medication administration apparatus determines the location and prescription schedule for each dose packet within the medication administration apparatus and provides an indication when a dosing event is scheduled.

5 Claims, 11 Drawing Sheets

(51) Int. Cl.
  *A61J 7/00* (2006.01)
  *A61J 7/04* (2006.01)
  *G16H 10/60* (2018.01)
(52) U.S. Cl.
  CPC ............ *G06F 19/00* (2013.01); *G06Q 50/22* (2013.01); *G16H 10/60* (2018.01); *A61J 7/0418* (2015.05); *A61J 2205/60* (2013.01)
(58) Field of Classification Search
  USPC ............................................................ 705/3
  See application file for complete search history.

(56) References Cited

U.S. PATENT DOCUMENTS

| | | |
|---|---|---|
| 2003/0200726 A1 | 10/2003 | Rast |
| 2004/0094564 A1* | 5/2004 | Papp ..................... A61J 7/0084 221/25 |
| 2005/0131733 A1* | 6/2005 | Lubow .................. G06Q 50/22 705/2 |
| 2006/0149416 A1 | 7/2006 | Mohapatra et al. |
| 2007/0078410 A1 | 4/2007 | Chiavetta et al. |
| 2007/0168228 A1 | 7/2007 | Lawless |
| 2008/0059228 A1 | 3/2008 | Bossi et al. |
| 2009/0024412 A1 | 1/2009 | Medvitz et al. |
| 2009/0294521 A1* | 12/2009 | de la Huerga .......... A61J 1/035 235/375 |
| 2012/0035760 A1 | 2/2012 | Portney |
| 2013/0131586 A1* | 5/2013 | Poutiatine ............. A61J 7/0038 604/59 |

OTHER PUBLICATIONS

Extended European Search Report dated Sep. 8, 2017 in European Patent Application No. 13772632.9.

* cited by examiner

METHOD, SYSTEM AND APPARATUS FOR MEDICATION THERAPY MANAGEMENT PROGRAMS

CROSS REFERENCE TO RELATED APPLICATIONS

This application is a national stage application under 35 U.S.C. 371 which claims the benefit of U.S. Provisional Application No. 61/619,880 filed on Apr. 3, 2012, the contents of which are incorporated by reference herein in their entirety.

BACKGROUND OF THE INVENTION

Field of the Invention

The present invention generally relates to embodiments of a method, system and apparatus for optimized management of medicine administration.

Description of the Related Art

Modern medicine relies heavily on the prescription of medications that are to be taken by the patient in an appropriate treatment regimen. A single prescription might involve a regimen such as: "Take 2 tablets, twice per day, morning and evening, after a meal." Patients who have complex medical problems commonly receive multiple prescriptions, which can lead to patient confusion and frustration. Many patients fail to faithfully follow the treatments that have been prescribed, especially when they face chronic "polypharmacy" regimens: the need to follow multiple prescription regimens at once. Poor compliance can lead to poor patient outcomes and increased healthcare costs in the form of expensive interventions and a higher incidence of hospitalization.

Poor adherence to prescription regimens can sometimes be partially addressed by the assistance of a nurse caregiver, to place medicines into organizing containers and then provide reminders and instructions to the patient in an ongoing manner. The problems with this approach are: (a) it is labor intensive and hence relatively expensive, (b) it works only when patients are in proximity to a nurse caregiver, (c) there's no easy or efficient way for medical professionals to monitor the patient's actual usage pattern unless they are continuously in proximity, and (d) any medications left unused are wasted.

Embodiments of the invention described herein address these concerns by providing a novel automated method, system and apparatus for organizing medications for the patient, capable of reminding them to take the medication, tracking their usage pattern, and enabling reclamation of any unused medications in a manner that meets FDA requirements for reuse.

SUMMARY

One embodiment of the invention includes a comprehensive, technology-enhanced pharmacy system for patients following a complex medication regimen. The system is capable of addressing multi-faceted factors which undermine treatment adherence in the target population. The system comprises: (1) a Computer Assisted Telephone Interview (CATI) platform capable of use by pharmacy personnel in structuring and guiding patient interactions; (2) a Multi-Source Integrated Treatment Database (MSITD) System including prescription information, drug information, real-time treatment status variables, and provider/patient preferences; (3) a set of Treatment Optimization Algorithms (TOA) configured to optimize patient medication regimens with respect to factors such as cost, safety, and lifestyle; (4) Personal Medication Cartridges (PMC) including customized medication packets and barcode or RFID technology for tracking; (5) a portable, mobile-technology enabled Drug Dispensing Device (DDD) capable of supporting polypharmacy medication regimens and the Personal Medication Cartridges; (6) a Treatment Incentive Program (TIP) for motivating patients to maintain treatment adherence; and (7) Treatment Portals for use by physicians, pharmacy personnel, and patients for monitoring treatment status as appropriate with respect to medication adherence, clinical symptoms, and overall treatment progress.

Embodiments of the invention include a portable medication dispenser (DDD) that may provide for tracking of dispensing activity and automating selection of medications to dispense. The DDD is configured to remind patients to take medications at the proper time, and then provide the correct medications. The apparatus includes a processing unit and sufficient information technology such that it can determine which medications should be dispensed at any particular time. The apparatus can also trigger reminders to the patient when medication administration is appropriate. For example, when a patient presses a "dispense" button on the DDD, the DDD can determine the appropriate medications to dispense at that time.

One embodiment of the DDD accomplishes the dispensing of medications by loading a Personal Medication Cartridge (PMC) which includes medication packets for any or all of the types of medication that the patient may need. Each packet may hold one or more pills, and each packet may be labeled with an identifying mark, such as, for example, a barcode. The PMC may include sealed and labeled blister packets with medication, where the labels include information specific to the prescription. In this case, the printed information may include a barcode, RFID, or similar that can be read by a barcode reader, RFID, or similar, that will be located within the DDD and a mechanism is provided such that the barcode reader can read and identify each of the packets loaded into the DDD via the PMC.

An embodiment of the apparatus may also comprise a dispensing mechanism such that when the barcode reader identifies the correct medication packet for dispensing, the dispensing mechanism can push the packet out of the device for use by the patient. After dispensing one medication packet, the DDD can repeat the process of using the bar code reader to identify the next packet that needs to be dispensed, and can employ its dispensing mechanism again to dispense that packet. The DDD may repeat this process until all needed packets are dispensed.

To supplement that patient's knowledge, the DDD may contain a screen that displays information about each packet as it is dispensed. This can include information such as "take this medication with food."

The DDD may also contain a system to transfer data to/from a remote system, such as a wireless modem. As packets are dispensed to the patient, the patient's usage pattern is recorded and eventually relayed to remote medical systems, such as the Master System included in embodiments of this invention.

Loading the DDD within the pharmacy is fairly straightforward. The DDD can perform automatic error checking routines to assure that the medications loaded are those expected for the patient. Specifically, when the PMC is loaded into the DDD, each packet contained in the PMC may be read by the barcode reader. This information can be corroborated with data in the MSTID system, and therefore pharmacy or caregiver errors can be caught. For example, if the wrong medications are provided to the patient, they will not be dispensed.

BRIEF DESCRIPTION OF THE DRAWING FIGURES

Certain embodiments in the present invention will be better understood when read in conjunction with the appended drawings wherein like reference numerals refer to like components. For the purposes of illustrating the device of the present application, there is shown in the drawings preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but merely to clarify a single illustrated embodiment of the invention. In the drawings:

DETAILED DESCRIPTION OF THE INVENTION

Figure 1:
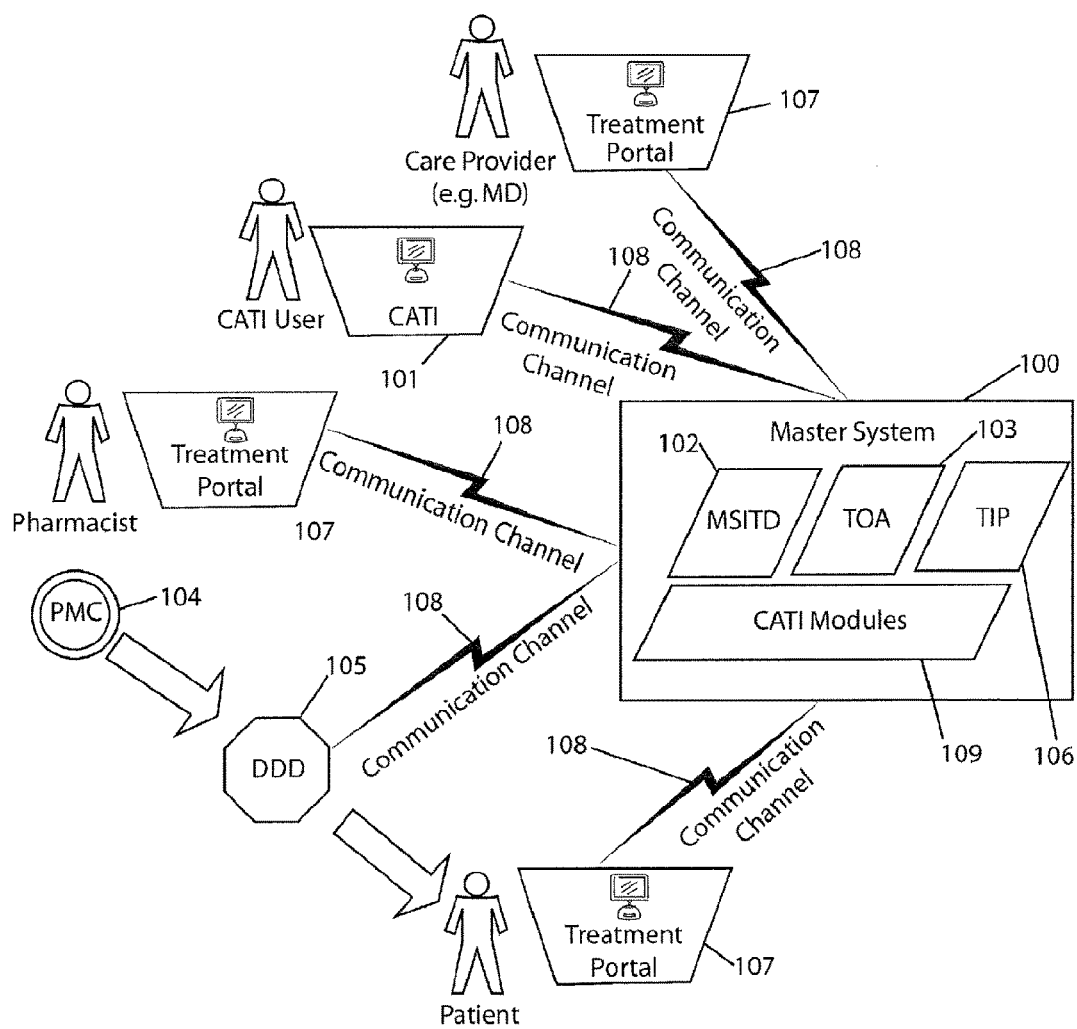
FIG. 1 is an exemplary diagram of the relationship between components of an embodiment of the invention.
Figure 2:
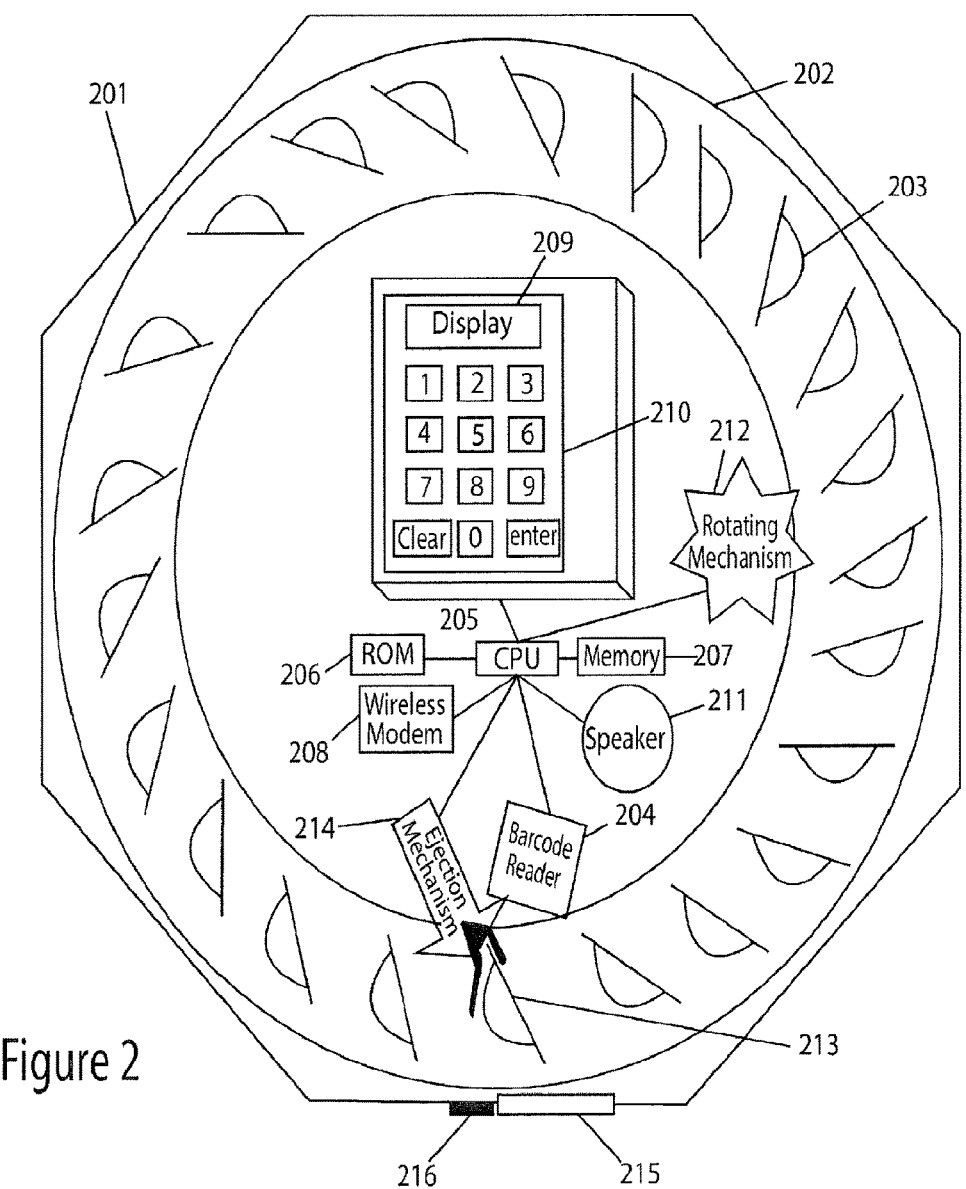
FIG. 2 is an exemplary diagram illustrating components of a drug dispensing device.

As shown in FIG. 1, components of one embodiment of a medication therapy management system (called DialogRX) include: A Master System 100; a Computer Assisted Telephone Interview (CATI) platform 101 for use by pharmacy personnel in structuring and guiding patient interactions; a Multi-Source Integrated Treatment Database (MSITD) System 102 comprising prescription information, drug information, real-time treatment status variables, and provider/patient preferences; and a set of Treatment Optimization Algorithms (TOA) 103 for optimizing patient medication regimens with respect to cost, safety, and lifestyle. The embodiment's components may interact synergistically to track and guide patient use of Personal Medication Cartridges (PMC) 104 which may contain individual medication dose packets labeled with barcodes or similar. The embodiment also comprises a portable mobile-technology enabled Drug Dispensing Device (DDD) 105 designed for holding and dispensing dose packets from the Personal Medication Cartridges at appropriate times and thus guiding patients through polypharmacy treatment regimens. A Treatment Incentive Program (TIP) 106 may be included, designed to motivate the patient and maintain treatment adherence. Communication with physicians, pharmacy personnel, and patients may be facilitated by Treatment Portals 107 for monitoring treatment status as appropriate with respect to medication adherence, clinical symptoms, and overall treatment progress. The Treatment Portals 107 and CATI platform 101 may connect with the Master System 100 via communication channels 108 that can be a secure internet connection (HTTP over TCP) or any other appropriate communication channel.

In some embodiments, the CATI platform 101 may be configured for use by pharmacy personnel or treatment management assistants to provide treatment assessments and interventions surrounding patients' medication regimens. The system may also include a series of "smart" CATI modules 109 that are part of the Master System 100. Modules 109 can be driven by real-time data for responding to key treatment-related events, such as the start of treatment, medication regimen changes, missed doses, refills, adverse reactions, poor adherence, or other medication-related problems. When an event occurs, a corresponding module may activate, detailing appropriate responses to pharmacy personnel or other users on a screen-by-screen basis. The activation may also include scripts for collecting additional information, administering assessments, educating patients, or teaching new skills and coping strategies. Pharmacy interviewers may read the script and/or questions posed on the computer screen and record any relevant answers or information directly into the computer. This information may then be entered into the MSITD 102 as described below and used as part of real-time branching logic sequences to continually guide the treatment process.

In some embodiments of the invention, the CATI platform 101 may also include CATI-Modules 109. CATI Modules 109 may include modules for providing Comprehensive Medication Reviews (CMR), Disease State Management, Patient Education, and Treatment-Related Problem Solving. One purpose of the CMR module is to comprehensively assess and optimize patients' medication regimen and related routines. A list of any or all of the patients' medications, including prescription and over-the-counter (OTC) medications, herbal therapies, and dietary supplements, along with related dosing parameters and guidelines (such as, for example, strength, frequency, missed dose rules, take with/without food, etc.) are reviewed and entered into the patient record and MSITD 102 described below. For use in the treatment optimizer algorithms, patients may also be asked to provide a "dosing convenience rating" for recurring daily and/or weekly activities, such as eating breakfast, coming home from work, going to bed, or other parts of patients' typical routines. Disease State Management modules may focus on assessing the clinical symptoms associated with patients' medical and psychiatric conditions, as well providing coping strategies for the common side-effects of the related medication treatment. Patient Education modules may focus on proactively enhancing patients' general disease and treatment knowledge, while TRPS modules may help providers respond to treatment-related problems as they occur in real-time, such as poor adherence rates, untimely cartridge swapping or refill requests, or other adverse events or treatment lapses.

In some embodiments of the invention, the MSITD System 102 is a master database, control, and reporting system for the apparatus, method or system. It may comprise prescription (Rx) information, drug information and patient-specific data. The drug data may include established dosing guidelines, restrictions, and warnings of commonly used prescription and OTC medications. The patient-specific data may include treatment-related data collected during enrollment in the DialogRX, including results of CATI-assessments, adherence rates, scheduling information, TIP points, and patient/provider preferences.

In some embodiments of the invention, Treatment Optimization Algorithms (TOA) 103 may be configured to utilizing MSITD data. The TOA 103 may comprise a series of treatment optimization algorithms which can be configured to optimize treatment outcomes, treatment cost, safety, and overall lifestyle. The TOA's cost optimizer may review the medications included in patients' regimen and identify potentially less expensive alternatives, such as generics. The TOA's safety optimizer may provide adverse reaction information and contraindication data for drugs included in the regimen. The TOA's lifestyle optimizer may use drug-information and patient scheduling/lifestyle preferences to devise a medication schedule that minimizes the total number of weekly dosing episodes, while simultaneously adhering to individual drug dosing guidelines and maximizing the convenience of individual dosing episodes from the patient point of view.

In some embodiments of the invention, a Patient Medication Cartridge 104 holds individual dose packets 203, which contain medications for the patient's regimen. FIGS. 2, and 4-11 illustrate exemplary designs and embodiments of the Drug Dispensing Device (DDD) 201 as discussed above. In this exemplary embodiment, the DDD is loaded with a PMC 202 made of a pre-formed, ring-shaped plastic carrier with "slots" arrayed on the ring in a circular pattern. It is envisioned, however, that other shapes and patterns may be utilized. The dose of a given prescription (typically 1 or 2 pills/capsules) is loaded into individual dose packets 203, and each packet is set into a slot on the PMC 201. Dose packets can be formed, for example, by loading pills into perforated plastic blister sheets that have indents for pills, sealing that blister sheet with a label, and then breaking the blister tray into individual packets along perforated lines. Labels may be printed such that dose packets display both printed information and a computer-readable mark, for example, a barcode, that identifies the medication contained within the dose packet. Dose packets would be configured to meet the most recent FDA standards of tamper-evident unit packaging, meaning that unused medication would be returnable in their original PMC packaging. Commercial providers of pharmaceutical packaging such as Medi-Dose have provided blister packaging with similar functionality.

The DDD 201 is designed to be easily loaded with a Patient Medication Cartridge (PMC) and can then read the identity of each dose packet contained in the PMC. The DDD 201 may resemble a portable CD player in shape, with a fold-open top and an open space inside for inserting a PMC 202, which in turn holds dose packets 203. In other embodiments, the DDD 201 may be configured in other shapes suitable for the invention. The DDD 201 further comprises a barcode reader (or RFID, or similar) 204 and an electronic system 217 with components known to one skilled in the art for logical control, user interface creation and control, and communication with the master system, including a CPU 205, ROM 206, read/write memory 207, and optional components such as a wireless modem 208, LCD screen 209, keypad 210, and speakers 211. Prescription and drug information may be stored locally or accessed at the MSITD System 102 via a modem device. The exemplary PMC can the rotated by a rotating mechanism 212 that is under the control of the CPU 205. This mechanism, which may contain a motor 219 and engage the PMC via gears 218, can rotate the exemplary PMC ring through at least 360 degrees so that all dose packets 203 can pass in front of the bar code reader (or RFID, or similar) 204 and be identified by the computing system. In some embodiments, the dose packets 203 may be oriented on the PMC such that a barcode label (or similar) 213 on the back of each packet can be seen by the barcode reader 204 that is mounted within the DDD 201. The DDD 201 may also comprise an ejection mechanism 214 which can eject the dose packets 203 via an exit slot 215. The ejection mechanism may be comprised of a geared motor 221 driving an ejection arm 222 that can push a packet out of the exit slot 215. The exit slot 215 may be monitored by a sensor 216 connected to the CPU 205, enabling the CPU 205 to determine when dose packets 203 have been both pushed outwards and then taken away by the patient. The rotating mechanism 212 may optionally contain a Geneva output gear interfacing with a Geneva planetary ring 220, such that the rotating mechanism 212 can induce step-by-step rotation of the Medication Cartridge 202. Thus each packet 203 will stop in front of the base code reader 204 and remain steady so that the barcode can be read reliably.

The information on the barcodes (or similar), combined with information local to the DDD computing system, or available via a remote connection to the Master System 100, can enable the DDD computing system to be aware of the exact nature of the medications loaded into the device. This information can be correlated with information available to the DDD (either locally resident or available remotely) about the patient's prescriptions and dispensing instructions for patient medications. Thus, the local computing system may have access to the information needed to dispense correct medications at the proper time. When the CPU determines that is it the proper time to dispense a particular dose packet, it instructs the rotating mechanism to advance the PMC to the correct position for dispensing of that dose packet. The correct position can be calculated by the CPU subsequent to initialization and reading of all packets in the PMC, and it can be further corroborated by using the bar code reader to confirm that the expected dose packet is in the exit position. The CPU can then initiate dispensing by activating the ejection mechanism. Various possible ejection mechanisms can be devised by one familiar with the art.

Figure 3:
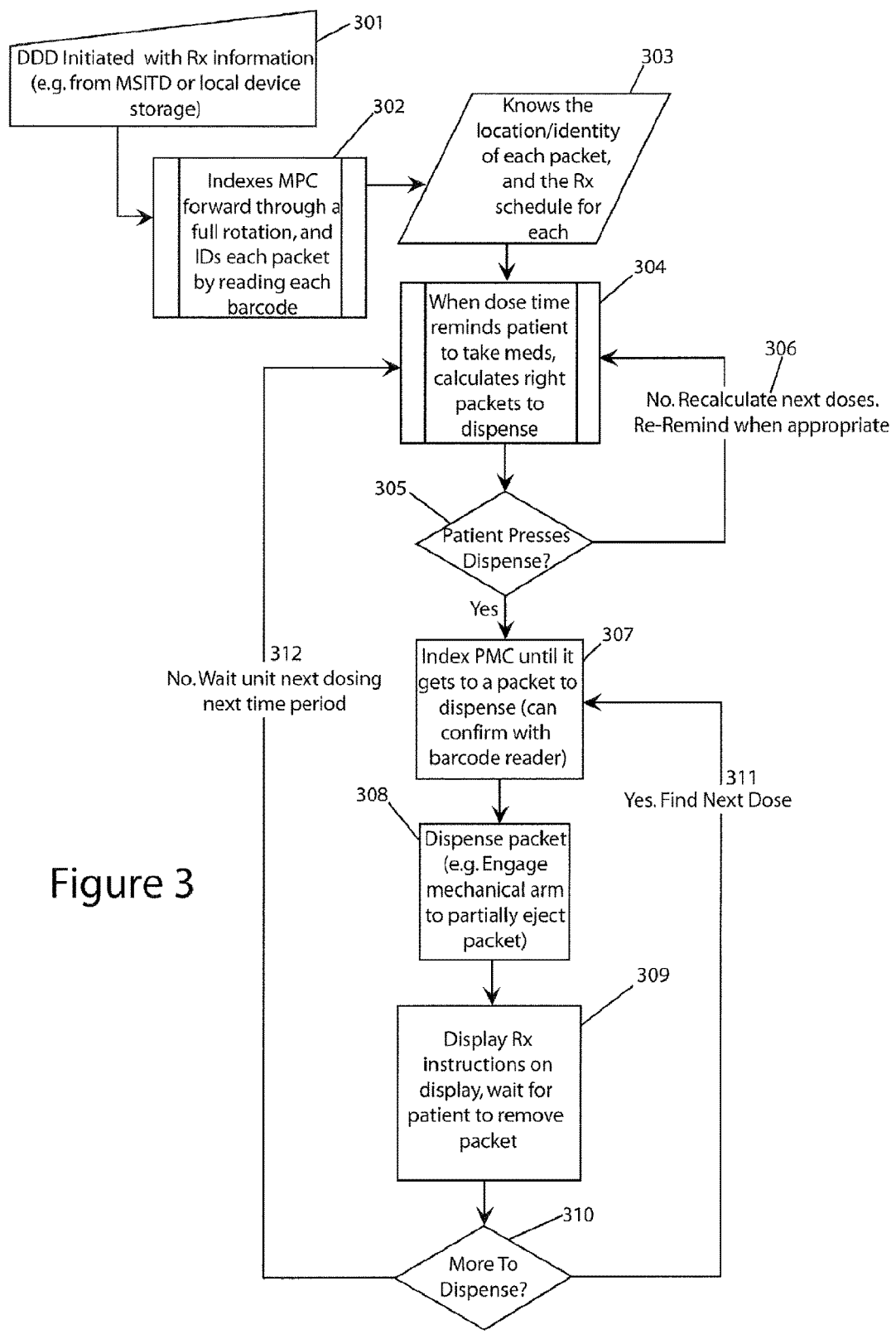
FIG. 3 is an exemplary flow diagram illustrating a dispensing process from an exemplary drug dispensing device.
Figure 4:
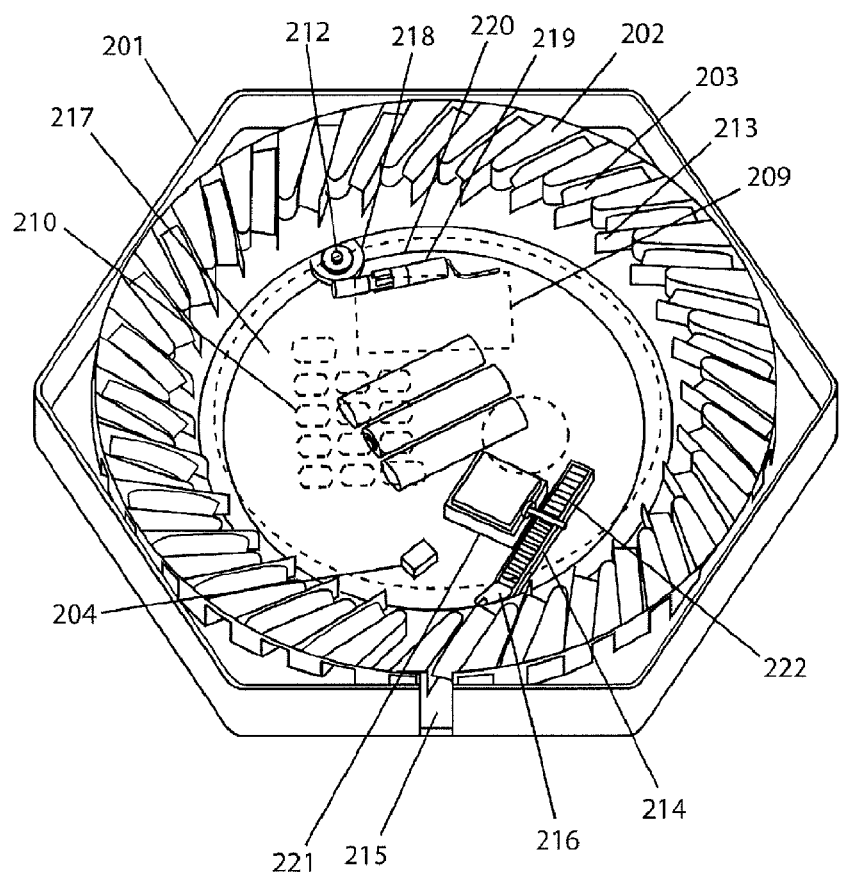
FIG. 4 is a perspective view of an exemplary embodiment of the DDD component and accompanying features.
Figure 5:
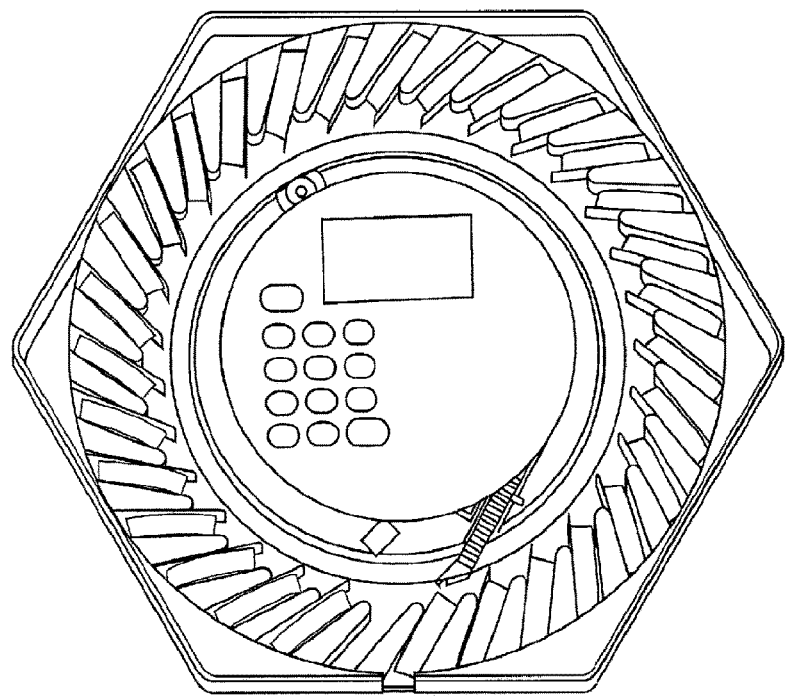
FIG. 5 is a top view of an exemplary embodiment of the DDD component featuring additional accompanying features.
Figure 6:
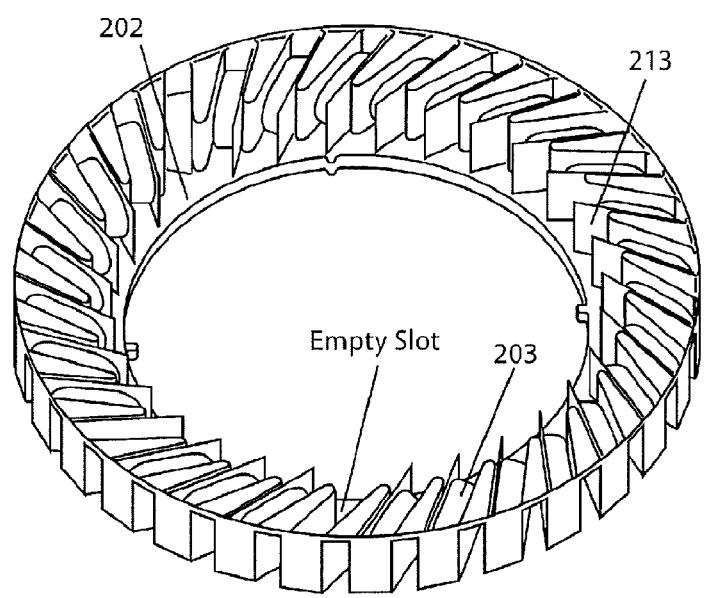
FIG. 6 is a perspective view of an exemplary embodiment of specific features of the DDD component.
Figure 7:
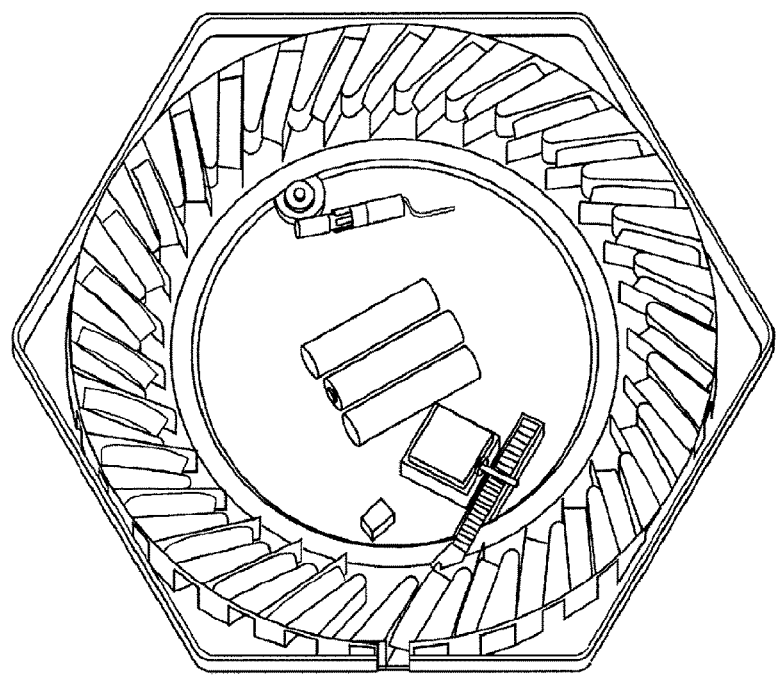
FIG. 7 is a top view of an exemplary embodiment of the DDD component featuring accompanying features.
Figure 8:
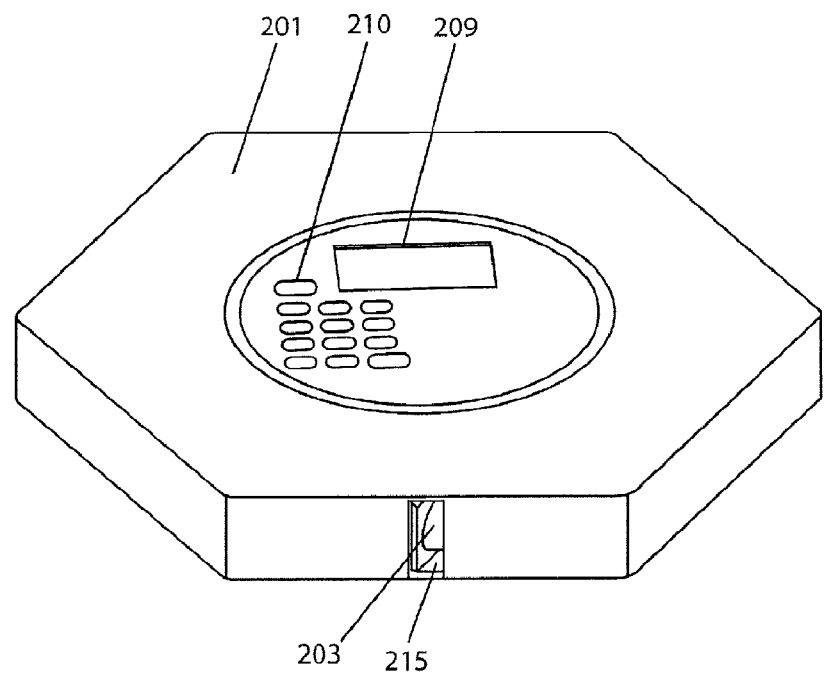
FIG. 8 is a perspective view of an exemplary embodiment of the DDD component.
Figure 9:
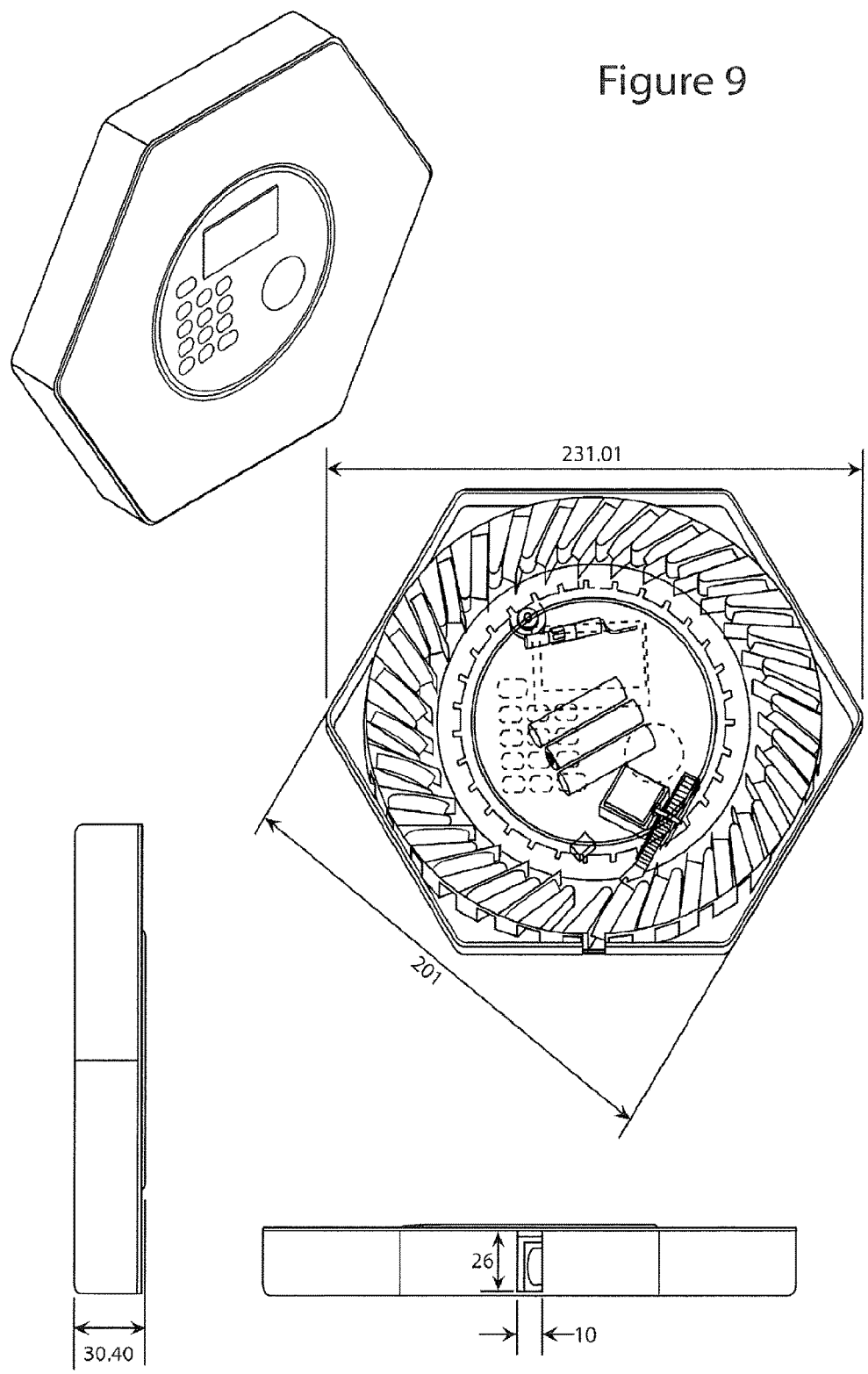
FIG. 9 is an exemplary engineering drawing of multiple perspectives of the DDD component and accompanying features according to an embodiment of the invention.
Figure 10:
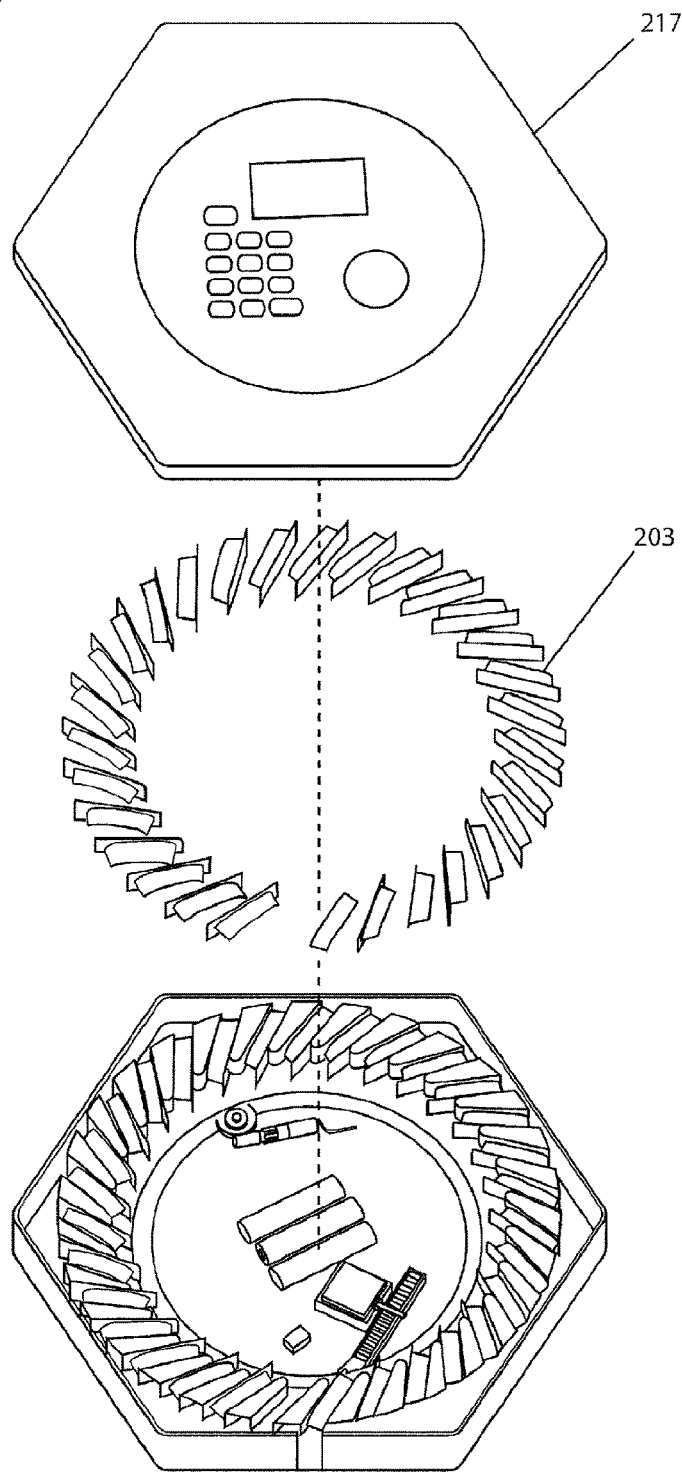
FIG. 10 is an exemplary exploded engineering drawing of the DDD component and accompanying features according to an embodiment of the invention.
Figure 11A:
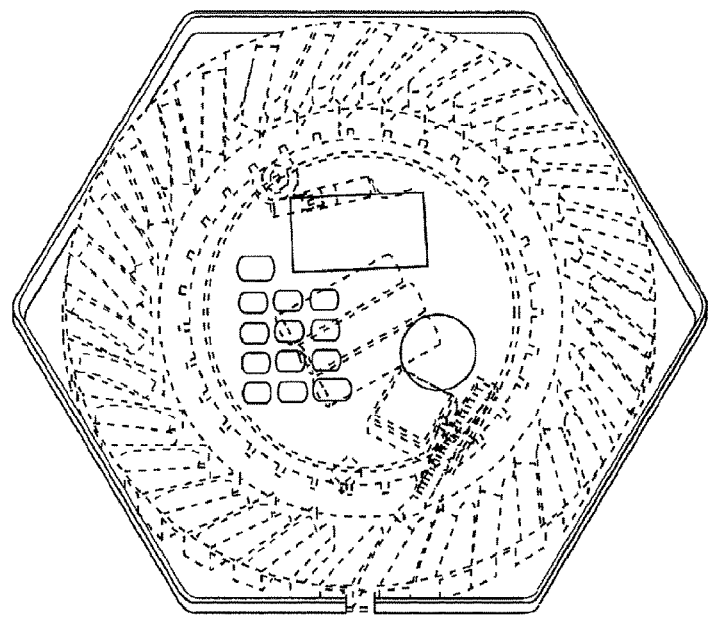
FIGS. 11a and 11b are top views of exemplary engineering drawings of the DDD component and accompanying features according to an embodiment of the invention.
Figure 11B:
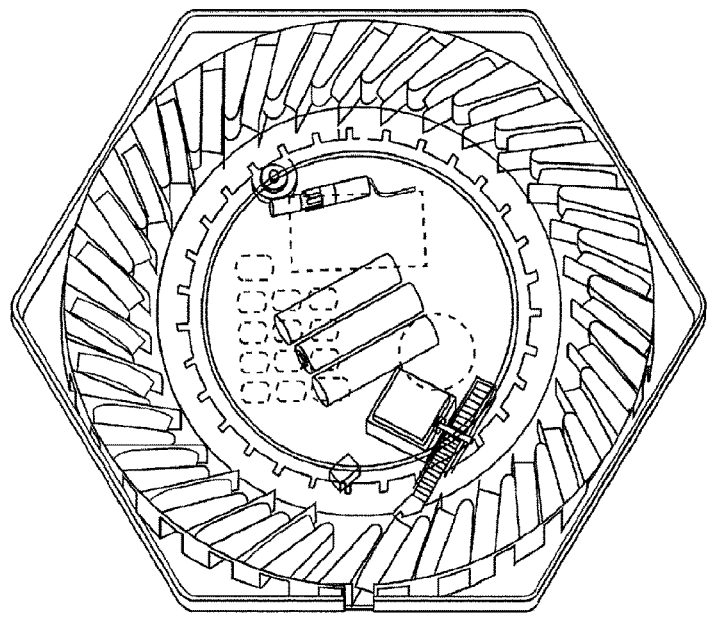

FIG. 3 illustrates an exemplary process followed by the DDD 201. The CPU triggers an initialization procedure 301 once the device is loaded with a PMC 202 whereby the ring-shaped PMC may rotate (for example, by 360 degrees or more) by the rotating mechanism 212. This enables the CPU 205 to sense the dose packets 203 loaded into the device and its location within the device, information which can be stored and used when the CPU needs to dispense a particular dose packet.

In step 303, the CPU correlates information about each packet found with drug information, prescription information, and patient information (whether retrieved from the Master System 100 or stored locally). The CPU can note discrepancies from the expected dose packets, and can initiate alerts via the display and/or via communication with the Master System. When a dosing episode 304 is scheduled, the device reminds users, for example, via visible message on the LCD, beeping, and/or vibrating, initiating a phone call via the Master System, etc. There embodiment may include reminder mechanisms known to one skilled in the art. The patient is asked to acknowledge this reminder by signaling a "Dispense" event, for example, by pressing a button on the DDD for "Dispense."

If, in step 305, the patient does not signal "Dispense," the device may wait a period of time and then return via path 306 to wait for another dosing episode. Along this path the device will recalculate, prior to the next dosing episode, the medications that need to be dispensed at the next reminder event. Some medications may need to be increased due to a missed dose, while others might not be increased, and hence a different set of dose packets may be selected for the next dispense event. The DDD's CPU, potentially in conjunction with instructions from the Master System 100, handles this recalculation.

When the patient does signal "Dispense," the system moves on to step 307 to index the PMC such that it is in position for dispensing of an appropriate dose packet. In the exemplary embodiment, the PMC 202 is rotated within the DDD by the rotating mechanism, under the control of the computing system, until a packet to be dispensed by the DDD comes into an exit position. This can be confirmed by the barcode reader (or similar) 204. This will be a position adjacent to an exit slot 215.

In step 308, the ejection mechanism 214 is initiated, which in the exemplary embodiment consists of a mechanical arm that pushes the packet partially out of an exit slot 215. A sensor 216 near the exit slot notes when the patient has grasped the packet and pulled into completely out, as the patient is instructed to do via the Display 209. After a dose packet 203 is partially ejected in step 308, written and/or audio prompts may guide the patient to proper usage (e.g. "take with water") for that medication in step 309. The DDD computing system may determine in step 310 if there is another dose packet 203 to dispense at this time, and if so via path 311 it calculates the next packet and returns to step 305 to find and dispense the next dose packet 203. If the CPU 205 determines that all required dose packets 203 have been dispensed at this time, it follows path 312 to calculate actions for the next dosing episode and waits for the appropriate time to initiate that dosing episode via step 304.

In this embodiment, the DDD and its computing resources can track and report the times at which the patient has take manual action to remove medication packets. Reporting to the Master System 100 can occur via modem 208, or can occur via other communication means as known in the art. Additionally, if the patient fails to take medication at an advised time, the DDD (and its associated computing resources, for example, the Master System 100 networked to the DDD) can recalculate the appropriate treatment path for the patient. For example, if the patient misses a Monday morning dose, the DDD may dispense different medications on Monday afternoon than it otherwise might have. Some medications, when doses are missed, need to be double-dispensed the next time, whereas others do not. This embodiment is configured to accommodate that complexity. Medications from the PMC that are ultimately not dispensed can be reclaimed and reused in future regimens.

In some embodiments, a Treatment Incentive Program (TIP) may comprise an incentive system incorporated into the DialogRX program to encourage proper system usage and ongoing treatment adherence. TIP points will be awarded to patients for completing assessment and/or intervention interviews with pharmacy personnel, completing educational materials, inserting the expected cartridges into the device in a timely manner, and for achieving specified levels of adherence as measured by the DDD system. Points can then be redeemed for discounts on various DialogRX products and services, including reduced drug costs, copayments, and/or subscription fees. Use of the TIP provides an important motivational impetus for maximizing patient adherence to all treatment-related protocols.

Treatment reports and treatment management features may be accessible to pharmacists, physicians, and patients as appropriate through secure, password-protected HIPPA compliant portals. Treatment reports may comprise a comprehensive list of patients' current medications and related dosing guidelines, current weekly dosing schedule, adherence records for all drugs across specified timeframes and/or particular dosing episodes, results of all assessments, completed CATI-interviews and/or other educational materials, and TIP totals. By themselves or with the assistance of pharmacy personnel, patients can view their own treatment reports, update scheduling preferences, change the planned time of future dosing episodes, reapply the optimizer algorithms, and set personal dosing prompt preferences. Portals may also be used for integrating physicians into the treatment process, whereby physician preferences for receiving treatment reports and/or alerts can be set (i.e., via phone call, mail, email, or, when available, automatic integration into EMRs).

Immediately after enrollment in the program, in some embodiments, patients may be administered a set of start-up CATI-modules, which may comprise a CMR interview as described above. As part of the CMR, TOAs can be used initially to optimize patients' medication regimen with respect to cost, safety, and convenience, resulting in a patient medication list and weekly dosing schedule. This information may then be used in the custom packaging process which involves packaging an initial supply of PMCs for a specified time period. A "starter" package is sent to patients consisting of the DDD, initial supply of PMCs, quick-start guide, and patient instructional DVD. The patient quick start guide may contain simple instructions and graphical illustrations of how to set-up/use the system and begin earning TIP points, while the DVD has a short video showing the different parts of the system in real world usage. A "starter" CATI-module is also available to pharmacy personnel for helping patients through the initial setup process as needed.

Once a patient account has been activated and the initial PMC loaded, the DDD is ready for use. When a dosing episode is scheduled, the device alerts patients and walks them through the dosing process as previously described. If dosing episodes are missed, the dispensing rules for upcoming episodes are adjusted accordingly based on the missed dose rules of all drugs included in the regimen, thereby making it possible to dispense double doses of individual drugs in subsequent dosing episodes as appropriate. To help facilitate advanced planning on the part of patients, LCD screen displays key information about the medication regimen on a regular basis, including time of next dosing episode, the number of remaining episodes available with the current PMC, and current TIP points. As patients use the device, adherence rates at the level of individual medications are calculated as described previously. When it is time for a PMC change, text/audio prompts guide patients through the process of swapping out the cartridges, with the barcode technology (or RFID, or similar) ultimately ensuring use of the correct cartridge and dispensing of only appropriate medication packets. PMCs with unused medication packets can be returned in supplied mailers for additional TIP points, while new PMCs are sent automatically to patients for refill purposes on a timely basis in accordance with their current prescriptions. Throughout the treatment, pharmacists administer CATI-modules as appropriate and update physicians and patients with treatment reports accordingly. Patients are also able to review their treatment reports and make changes to their regimen through access to their personal portal.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps and/or functions described herein is not to be considered implying a specific sequence of steps to perform the process. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Although the present invention has been described and illustrated in the foregoing exemplary embodiments, it is understood that the present disclosure has been made only by way of example, and that numerous changes in the details of implementation of the invention may be made without departing from the spirit and scope of the invention.

What is claimed is:

1. A method of administering a medication therapy program comprising:
   utilizing a master system having a treatment database configured to retain at least one of medication information, prescription information and patient information;
   utilizing a medication administration apparatus configured to wirelessly communicate with the master system and containing a plurality of medication dose packets each having a distinct computer-readable identification mechanism, and containing an identification mechanism reader;
   the medication administration apparatus:
      identifying individual medication dose packets using the identification mechanism reader;
      corroborating identification mechanisms associated with identified medication dose packets with at least one of medication information, prescription information, and patient information, thereby confirming the medication dose packets are expected medication dose packets;
      reporting in real-time to the master system discrepancies between the plurality of medication dose packets and at least one of medication information, prescription information, and patient information;
      determining the location and calculating a dispensing time for at least one medication dose packet within the medication administration apparatus;
      locating the correct medication dose packet to dispense at the calculated dispensing time;
      positioning the correct medication dose packet to be dispensed at the correct dispensing time;
      determining when dispensing of a particular read medication dose packet is completed;
      reporting in real-time to the master system treatment-related events, including a non-completed dispensing of a medication dose packet.

2. The method of administering a medication therapy program of claim 1, further comprising providing an indication that a dosing event is scheduled and waiting for a patient to request dispensing of a dose packet.

3. The method of administering a medication therapy program of claim 1, further comprising recalculating dosing event information based on a patient's deviation from a predetermined dosing schedule.

4. The method of administering a medication therapy program of claim 1, further comprising providing visual or audio prompts to the patient to guide proper medication administration.

5. The method of administering a medication therapy program of claim 1, further comprising communicating treatment reports to at least one of a physician, pharmacist and patient.

* * * * *